United States Patent [19]

Morgan

[11] 4,112,737

[45] Sep. 12, 1978

[54] TRANSFORMER FAULT DETECTION

[75] Inventor: James E. Morgan, Kirkland, Canada

[73] Assignee: Morgan Schaffer Corporation, Montreal, Canada

[21] Appl. No.: 791,512

[22] Filed: Apr. 27, 1977

[51] Int. Cl.² .................................. G01N 7/10
[52] U.S. Cl. ........................................... 73/23
[58] Field of Search ............... 73/19, 23; 55/158; 23/232 R, 254 R

[56] References Cited

U.S. PATENT DOCUMENTS

| 3,438,241 | 4/1969 | McKinley | 73/19 |
| 3,680,359 | 8/1972 | Lynch | 73/23 |
| 3,866,460 | 2/1975 | Pearce | 73/19 |
| 3,871,228 | 3/1975 | Weiss | 73/19 |
| 3,884,814 | 5/1975 | Vogt et al. | 55/158 |
| 3,976,450 | 8/1976 | Marcote et al. | 73/23 |

Primary Examiner—Stephen A. Kreitman
Attorney, Agent, or Firm—Swabey, Mitchell, Houle, Marcoux & Sher

[57] ABSTRACT

Apparatus and method for detecting fault gases in oil insulated transformers including a cell adapted to be located in the fault gas environment, the cell being hollow and including a gas-permeable wall but impermeable to liquids, means for flushing the contents of the cell into an analytical measuring device for determining the concentration of the specific fault gas in the cell.

8 Claims, 5 Drawing Figures

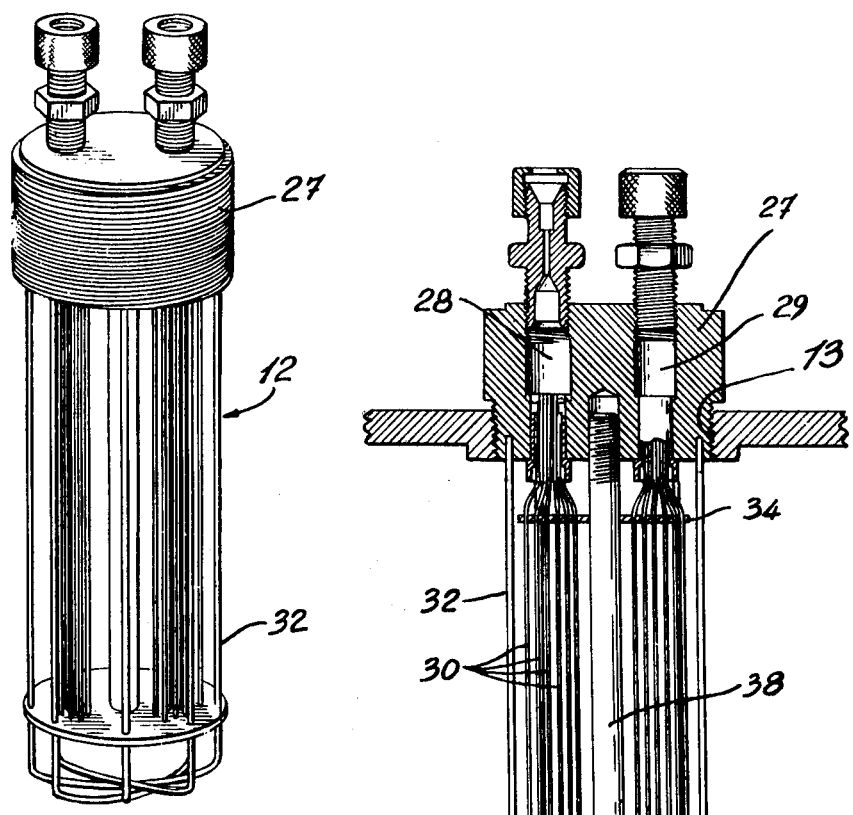

TRANSFORMER FAULT DETECTION

BACKGROUND OF THE INVENTION

1. Field of the Invention

The present invention relates to the detection of gases produced by incipient faults in electrical equipment, and more particularly in electrical transformers.

2. Description of the Prior Art

It has long been recognized by the electrical industry that abnormal electrical and thermal stresses in electrical apparatus are invariably accompanied by degradation of the surrounding insulating material. In oil/paper insulating systems, this degradation is accompanied by the production of a number of gases. These are principally hydrogen, carbon monoxide and carbon dioxide and low molecular weight hydrocarbons. The rate of generation of these gases and their composition is a function of fault severity, i.e., rate of energy dissipation and temperature, and of fault type (hot spot, arcing, partial discharges, etc.).

At the high generation rates characteristic of an actual fault, this phenomenon has been utilized for many years to activate gas sensitive alarms and protective relays. However, it has also been recognized that reliable detection of fault gases, before the generation rate becomes large enough to activate such device, can provide invaluable early warning of incipient fault development.

Detectors have been developed which continuously monitor gases resulting from incipient faults, such as in U.S. Pat. No. 3,680,359, Lynch, 1972. However, the monitor described in this patent appears limited to gas cushioned transformers and is based on detection of hydrogen by measurement of the thermal conductivity of the gas which comprises the gas cushion. Such detection is made possible by the fact that hydrogen has a much higher thermal conductivity than the nitrogen which is the main component in the gas cushion. The monitor includes means to continuously test the thermal conductivity, and as the thermal conductivity of the gas blanket increases above the base conductivity, a warning will be emitted by the monitor. The Lynch type of monitor does not appear useful in a completely oil filled apparatus such as conservator and diaphragm sealed power transformers or in sealed instrument transformers.

In U.S. Pat. No. 3,559,457, Collins, 1971, there is described a hydrogen detector for use in a transformer tank which includes a tube formed of palladium alloy which will expand in the presence of hydrogen. Indicator means are connected to the tube to display the amount of its axial expansion. This device has probably relatively low detectability and is probably relatively insensitive. It would also appear that the hydrogen detector of this patent must be used in a gaseous environment, such as in the nitrogen cushion over the oil insulator in a transformer. It is not believed that the device shown in this patent could be utilized in an oil sealed transformer to detect dissolved hydrogen.

SUMMARY OF THE INVENTION

It is an aim of the present invention to provide a probe or detection unit which is capable of operation when immersed either in a liquid, such as insulating oil, or in a gaseous system, such as the gas cushion above the insulating oil in a transformer, and wherein fault gases can be collected and subsequently measured.

A construction in accordance with the present invention includes a probe having a cell adapted to be located in a potential incipient fault gas environment, the cell being hollow and including a wall, a portion of which is permeable to gases but impermeable to liquids, means for flushing the contents of the cell into an analytical measuring device for determining the concentration of specific fault gases in the cell.

In a more specific embodiment of the present invention, there is provided a probe adapted to be inserted within the insulating oil in the transformer tank, the probe including a bundle of hollow tubes forming cells connected at each end to respective manifold means, each tube being permeable to gases but impermeable to liquids, means for connecting an analytical measuring device to the manifolds, and means for flushing the probe contents into a measuring device for determining the composition of the probe gas.

Gases dissolved in the transformer oil diffuse through the permeable walls into the probe until a condition of dynamic equilibrium is established. Each gas behaves independently and the time necessary for a particular gas to reach its equilibrium partial pressure within the probe will be dependent upon the permeability of the probe walls for that particular gas. The time necessary to reach equilibrium is also directly proportional to the internal volume of the probe but inversely proportional to the surface area of the permeable walls. These latter factors are independent of the nature of the gas so that short equilibration times are favored by thin, highly permeable walls, and a large surface-to-volume ratio.

The equilibrium partial pressure of a particular gas is directly proportional to the concentration and inversely proportional to the solubility of the gas in the oil. Factors which may affect the rate of attainment do not affect the final equilibrium pressure so that the composition of the gas within the probe is related in a reproducible, functional manner to the dissolved gas composition. It is noted, however, that the inverse dependence on solubility results in the probe gas being relatively enriched in the less soluble components and depleted in the more soluble ones. This can be advantageous if detection of a specific gas of low solubility (such as hydrogen) is desired.

Such a probe will function equally well when immersed in a gaseous environment, e.g., the gas space at the top of a so-called "gas blanketed" transformer. In this case, the equilibrium partial pressures within the probe are exactly equal to the partial pressures in the gas blanket. If the gas blanket itself is in equilibrium with the oil, then the relationship between the dissolved gas concentrations and the partial pressures in the gas blanket (and hence also inside a probe immersed in the gas blanket) are the same as would exist for a probe immersed directly in the oil.

Transfer of the probe contents to an analytical device is most easily accomplished by sweeping the probe contents out with a carrier gas. The use of a carrier gas, plus the ease of separation and detection of fault gases by gas chromatographic methods makes this analytical technique the method of choice for analyzing the probe contents. Thus, in principle, the analytical device need only be a portable gas chromatograph which can be temporarily connected to the probe to perform the required analysis.

When the probe is operated in the manner described above, it is apparent that a certain minimum period of time must be allowed between tests so that equilibrium can be reestablished since the act of testing leaves the probe filled with carrier gas. In some instances continuous monitoring would be advantageous and this can be achieved with the present invention by allowing a continuous flow of carrier gas to pass through the probe with continuous monitoring of specific components in the exiting carrier gas. However the concentration of a particular component in the continuously flowing carrier gas will be much lower than the equilibrium concentration and will also be dependent upon many operational and physical parameters.

It will be appreciated from the foregoing that the probe may be regarded as a universal, non-selective sampling device potentially allowing detection and measurement of any, or all, fault gases dissolved in the transformer oil or present in the gas space above the oil. The completeness of such analyses will be determined only by the capabilities of the analytical device rather than any inherent limitations of the probe.

Having thus generally described the principles upon which the probe acts as a sampling device, it is necessary to discuss its adaptation and use with particular analytical devices, more specifically those based upon gas chromatographic principles. For the purposes of gas chromatographic analysis the probe may be regarded as exactly equivalent to the sampling loops commonly used with conventional laboratory gas chromatographs. The major difference between the probe and a normal sampling loop is that the probe is self filling and only requires insertion into the chromatographic gas flow circuit in order for a test to be conducted.

In the normal mode of operation of a gas chromatograph, the gas sample volume must be well defined and reproducible and its size must not exceed certain limits with relation to the volumetric flow rate of the carrier gas. A typical ratio of sample volume to carrier flow rate would be 0.01 minutes. In a portable chromatograph, weight and size limitations limit carrier gas flows to the order of 10–20 mls per minute thus automatically restricting the allowable sample size (probe volume) to about 0.1–1.0 ml. If these conditions are met, the peaks on the resulting chromatogram will be directly proportional, both in peak area and in peak height, to the quantities of the individual components contained in the sample gas. Thus peak heights (or areas) can only be converted to concentrations or partial pressures if the total sample size is known.

The requirement that the sample volume be well defined and reproducible necessitates the presence of valves, or some other type of closure on the inlet and outlet ports of the probe. Manually operated valves, mounted directly on the probe, can be used if the probe is accessible. If the probe is mounted in an inaccessible location requiring extension leads to an accessible connection station, remotely operated valves would be required. Valves mounted at the accessible ends of the extension leads would not be satisfactory because this would add an unacceptable extra volume to the probe. This extra volume in the extension leads, because of its physical configuration, would take an unacceptably long time to reach complete equilibrium throughout. The net effect of extension leads terminated with valves would be that the effective volume of the probe would no longer be either constant, reproducible or acceptably small.

An alternative to mechanical valves in effectively defining and limiting the volume of the probe can be achieved by attaching metal extension leads to the probe, into which are inserted gas permeable sections (diffusers) a short distance from the probe. Fault gases diffuse into the probe in the normal manner but will also diffuse down the metal extension leads. Upon reaching the gas permeable section, the fault gases diffuse out into the atmosphere thus automatically limiting the effective volume of the probe. Additional extension leads from the diffusers to the accessible connection station do not form part of the probe volume and hence they can be as long as necessary (within constraints imposed by considerations of resistance to carrier gas flow). Short, highly efficient diffusers are preferred so that the fault gas concentrations are reduced essentially to zero close to the ends of the metal leads extending from the probe. Such diffusers would typically consist of a bundle of narrow bore, thin walled tubes made of gas permeable material such as polytetrafluoroethylene or silicone rubber. Alternatively, a longer, less permeable, single tube can fill the role of diffuser, a practical solution being to connect the probe to the accessible connection station by gas permeable, rather than metal extension leads.

The length and internal diameter of the metal extension leads between the probe and the diffusers and the length and efficiency of the diffusing sections of the leads must be chosen so that:

(a) the effective probe volume is kept within acceptable limits (b) diffusive flow down the leads is sufficiently low not to affect significantly the equilibrium concentrations within the probe (c) loss of fault gases when the probe contents are swept through the diffusers during a test are acceptably low.

Virtually all of the difficulties associated with the normal mode of gas chromatographic analysis can be eliminated by using a sample volume which greatly exceeds the normal requirement. In this mode the gas chromatograph is overloaded to the point where the peaks in the resulting chromatogram become flat topped and no longer increase in height with increasing sample size. The height of these flat topped peaks is directly proportional to the concentration (rather than the quantity) of the individual components within the sample. In this mode of analysis the probe volume only has to meet the necessary minimum requirement to produce flat topped peaks. Additional volume contributed by variable amounts of diffusion down extension leads, constructional tolerances in the probe itself, etc., have no effect on peak heights thus eliminating the need for valves or other devices for defining the probe volume. This is the preferred configuration of probe and test set in the present invention.

BRIEF DESCRIPTION OF THE DRAWINGS

Having thus generally described the nature of the invention, reference will now be made to the accompanying drawings, showing by way of illustration, a preferred embodiment thereof, and in which:

FIG. 3 is a perspective view of the probe;

FIG. 4 is an axial cross-section of the probe shown in FIG. 3; and

DESCRIPTION OF THE PREFERRED EMBODIMENTS

Figure 1:
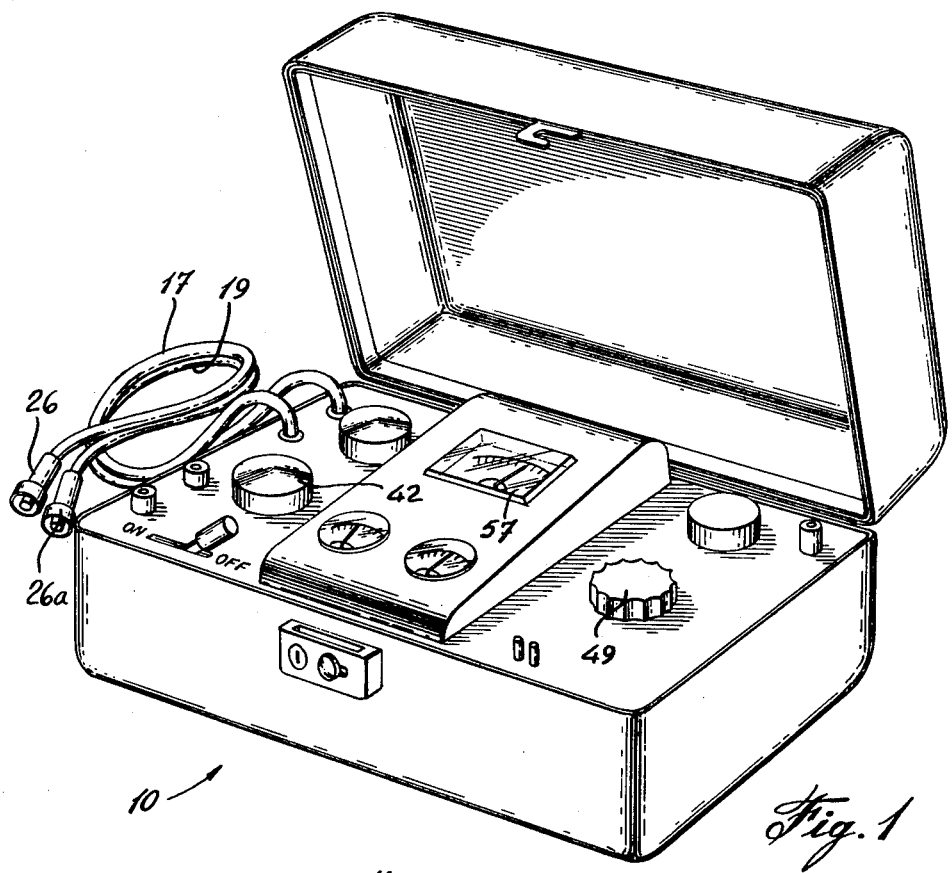
FIG. 1 is a perspective view of a typical analytical measuring device for use with the probe of the present invention.
Figure 2:
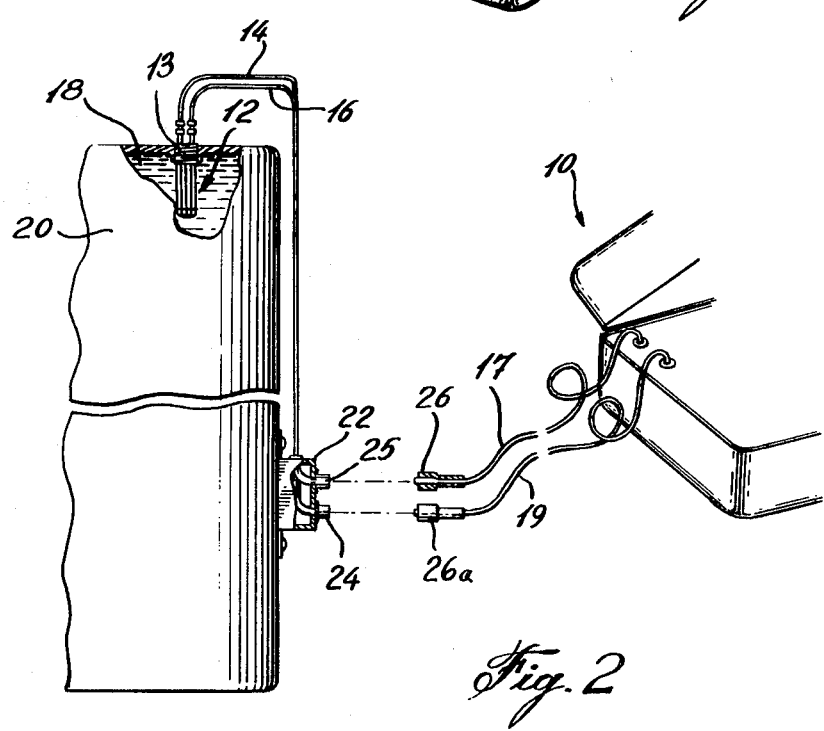
FIG. 2 is a fragmentary elevational view of a typical insulating oil transformer tank with a probe installed for monitoring the insulating oil and a fragmentary perspective view of an analytical measuring device being shown adjacent the tank.

Referring now to the drawings, and particularly to FIGS. 1 and 2, there is shown a typical transformer tank wall 20 in which insulating oil 18 is present. An analytical measuring device 10, which includes a portable casing, is adapted to be momentarily connected to the probe 12.

The probe 12 is provided within the confines of the tank wall 20 by screwing into a suitable port 13 in the tank wall 20. The probe 12, as shown in FIGS. 3 and 4, includes a threaded plug 27 adapted to be screwed into the port 13. A protection cage is provided which is made up of a plurality of spaced-apart nylon rods 32. A center rod 38 is connected to plug 27 and mounts support discs 34 and 36.

The plug 27 includes a pair of parallel extending bores in which are provided manifolds 28 and 29. A plurality of fine hollow tubes 30 extend from and communicate at each end with a manifold 28 and 29 respectively. The tubes 30 must be connected in an oil-tight manner with the plug 27. Each one of the tubes 30 is made of thin walled material which is permeable to small molecule gases but is not permeable to liquid. A typical material, and the material which is used in the present embodiment, is polytetrafluoroethylene. The choice of polytetrafluoroethylene as the tube material was made based on the fact that it is physically and chemically inert to hydrocarbon oils but at the same time exhibits high permeability to gases, particularly hydrogen.

The tubes 30 pass through the support discs 34 and 36 such that they are held spaced apart and are supported.

In the set-up illustrated in FIG. 2, elongated tubes 14 and 16 extend from the manifolds 28 and 29 to the connecting station 22. Quick disconnect plugs 24 and 25 would be provided at the end of leads 14 and 16 to receive mating plugs 26 and 26a on leads 17 and 19 from test set 10. The leads 14 and 16 can be made of metal, such as copper or stainless steel. An internal diameter of 0.66 mm and lengths between 2 and 6 meters have been found to be accetable.

In a typical embodiment, the protective cage 32 included eight nylon rods of 1.59 mm diameter. The length of the cage 32 was 11.00 cm with an approximate diameter of 2.5 cm. There were 42 polytetrafluoroethylene tubes 30 provided, and the length of the loop between the manifolds 28 and 29 respectively was approximately 25 cm. The outside diameter of each tube 30 was 0.75 mm while the thickness of the wall was 0.15 mm. The total tube volume was approximately 1.7 cc.

The manifolds 28 and 29 include chambers enlarged such that the total effective volume of the probe including the volume of the tubes 30 would be approximately 4 cc.

Figure 5:
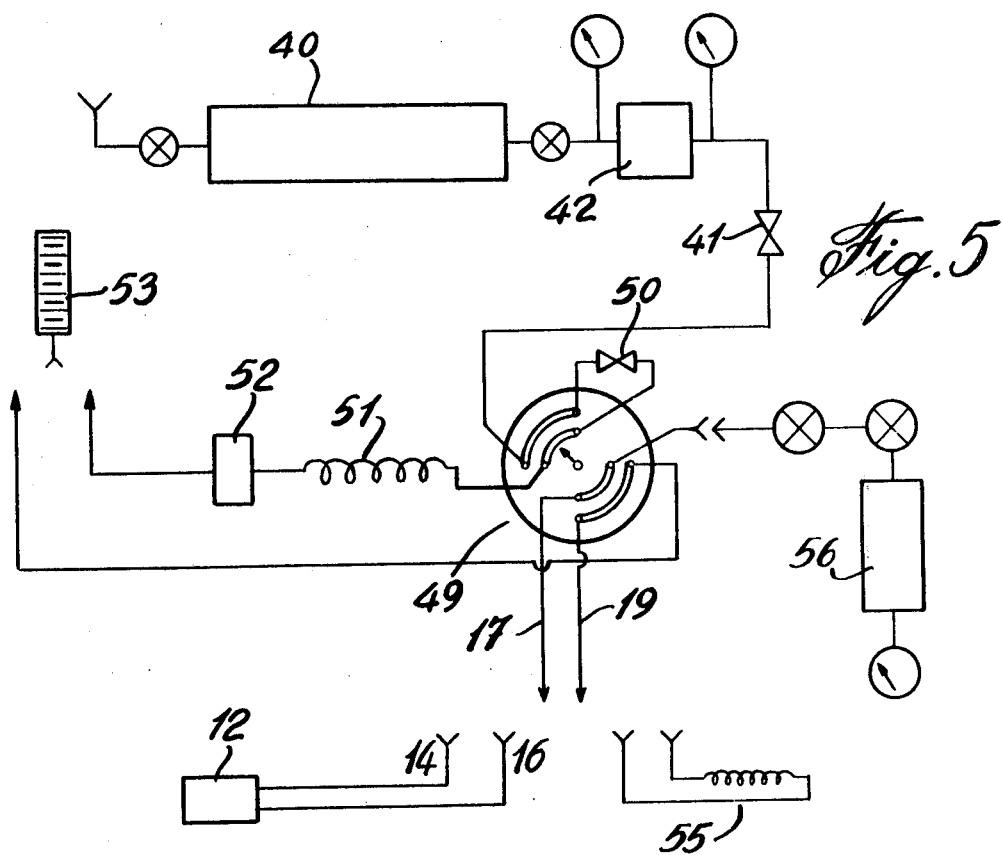
FIG. 5 is a typical schematic view of the analytical measuring device when it is not connected to the probe.

Referring now to FIG. 5 which shows a schematic of the test set 10, there is shown a stainless steel cylinder 40 containing pressurized carrier gas. The cylinder 40 can be quickly refilled without its removal from the test set 10 by direct attachment to a standard cylinder of carrier gas. As shown in the flow diagram of FIG. 5, the carrier gas from the cylinder 40 passes through a pressure regulator 42 and a flow restrictor 41. The carrier gas then passes to an eight port switching valve 49. In the standby position, the carrier gas is routed through restrictor 50 whose resistance approximates that of a typical probe. Gas then passes through the analytical column 51. After passing through the detector cell 52, the carrier gas flow is monitored by a rotameter type flow meter 53.

Initiation of the test sequence requires first attaching the test leads 17 and 19 to the leads 14 and 16 of probe 12, after which a 90° rotation of the switching valve 49 places the probe 12 into the gas flow circuit; thus, the carrier gas sweeps the probe contents into the analytical column 51. After completion of the analysis, the switching valve 49 is returned to the standby position, and the test leads 17 and 19 are disconnected from the probe 12.

Calibration of the test set is accomplished by connecting the test leads 17 and 19 to an internal loop 55 which can be filled by flowing a calibration gas contained in a separate cylinder 56 in the test set, through it while the switching valve 49 is in the standby position. Rotation of the switching valve 49 to the test position then sweeps the calibration gas into the analytical column 51 as in a normal test. Direct calibration in this manner simultaneously calibrates both the gas flow and electronic circuitry.

In a preferred embodiment the test set has been designed for the detection and measurement of hydrogen in the probe gas. In this embodiment the detector is a thermal conductivity cell utilizing thermistors as detector elements. The output from the detector cell is amplified and presented on a panel meter 57 calibrated to read directly in parts per million (ppm) of dissolved hydrogen. The analytical column is filled with Molecular Sieve 5A and the carrier gas is dry synthetic air supplied at a rate of approximately 15 cc per minute. Hydrogen is the first component to elute from the column followed by oxygen, argon, nitrogen, methane, carbon monoxide and ethane. Of these components, oxygen and nitrogen are not detected because of the use of air as a carrier. Methane, carbon monoxide and ethane, because of their long elution times and the closeness of their thermal conductivities to that of air, in practice are also not detectable. Argon, which is not present in the synthetic air used as a carrier, produces a negative signal. The only significant positive signal is produced by hydrogen which, because of its rapid elution and very high thermal conductivity, is easily detectable in very low concentrations. (The preferred embodiment of probe and analytical device described here can readily detect as little as 10 parts per million by volume of dissolved hydrogen in transformer oil).

An electronic circuit (not shown) is included in this embodiment which retains the maximum positive output from the thermal conductivity cell for as long as the switching valve 49 is in the test position. This ensures that the transient hydrogen signal is not lost if the operator's attention is distracted from the meter or if a test reading goes off scale. The retained reading is destroyed automatically as soon as the switching valve 49 is returned to the standby position.

I claim:

1. In electrical equipment containing insulating oil wherein fault gases may be generated, the improvement comprising means for detecting and measuring said fault gases, said means comprising a cell adapted to be located in a potential fault gas environment within said electrical equipment, said cell including an inlet manifold and an outlet manifold, a plurality of elongated hollow tubes, each of said tubes communicating respectively with said inlet and outlet manifolds, each of said tubes being permeable to gases but impermeable to liquids, hollow extension leads extending from said inlet and outlet manifolds, a portable analytical measuring device, means for removably connecting said hollow extension leads to respective inlet and outlet conduits in said measuring device, said measuring device including a gas chromatograph analyzing means, means in said portable measuring device for passing a carrier gas through said inlet conduit, through said hollow tubes, and through said extension leads and said outlet conduit for flushing into said gas chromatograph analyzing means a sample gas which is allowed to come to equilibrium in said cell, the minimum volume of sample gas in said cell at equilibrium being defined by the internal volume of said plurality of hollow tubes and said manifolds, said minimum sample gas volume being sufficiently large so that individual gases separated by said gas chromatograph analyzing means temporarily attain constant concentrations in said carrier gas, said constant concentrations being independent of said sample gas volume so that concentrations of individual fault gases in said sample gas can be measured without consideration of the actual volume of said sample gas.

2. An apparatus as defined in claim 1, wherein said cell is fixedly mounted within the insulating oil of said electrical equipment and said hollow extension leads project outwardly of the housing of said electrical equipment for easy access for connecting and disconnecting said portable measuring device.

3. An apparatus as defined in claim 1, wherein said portable measuring device includes storage means for storing said carrier gas under pressure, valve means for communicating said carrier gas storage means with said inlet conduit when required for flushing the sample gas from the cell, additional valve means for allowing said sample gas and said carrier gas to pass through the gas chromatograph analyzing means when required.

4. Apparatus as defined in claim 1, wherein the cell includes a plug which is threaded for connection with a similarly threaded aperture in the transformer wall, the plug including a pair of manifolds which communicate with a pair of leads respectively communicating outwardly from said plug.

5. Apparatus as defined in claim 4, wherein the hollow tube walls are made out of polytetrafluoroethylene.

6. Apparatus as defined in claim 5, wherein there are 42 hollow tubes forming the cell, each tube having a length of approximately 25 cm. and with an outer diameter of approximately 0.75 mm. and with a wall thickness of approximately 0.15 mm., such apparatus having a collective total internal volume, including the manifolds, of approximately 4 cc, such apparatus having provision for the connection of metal extension leads, such leads having an internal diameter of less than 0.7 mm.

7. A method of detecting and measuring the presence of fault produced gases in an oil-filled electrical equipment comprising the steps of installing a cell made up of hollow tubes with walls permeable to fault gases but impermeable to liquids within the equipment containing the oil, allowing the sample gas to come to equilibrium within the cell with its environment exterior of the cell and at equilibrium flushing the sample gas with a pressurized carrier gas through a portable analytical measuring station, passing the sample gas through a gas chromatograph analyzing device within said measuring station, measuring the concentration of specific gases within the sample gas, separating the components in the carrier gas whereby the components in the carrier gas attain a temporary state of constant concentration, disconnecting the portable measuring device from the cell and allowing the sample gas within the cell to be restored to equilibrium.

8. The method defined in claim 7, in which the specific component measured is hydrogen.

* * * * *